United States Patent
Krieger et al.

(10) Patent No.: US 10,022,218 B2
(45) Date of Patent: Jul. 17, 2018

(54) TRICUSPID REGURGITATION MODEL AND METHODS OF EVALUATING INTRALUMINAL MEDICAL DEVICES

(71) Applicant: Cook Medical Technologies LLC, Bloomington, IN (US)

(72) Inventors: Joshua Krieger, Bloomington, IN (US); Sean Chambers, Bloomington, IN (US); Zachary Berwick, Indianapolis, IN (US); Ghassan Kassab, Zionsville, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 433 days.

(21) Appl. No.: 14/622,165

(22) Filed: Feb. 13, 2015

(65) Prior Publication Data
US 2015/0230947 A1 Aug. 20, 2015

Related U.S. Application Data

(60) Provisional application No. 61/939,780, filed on Feb. 14, 2014.

(51) Int. Cl.
*A61F 2/06* (2013.01)
*A61F 2/24* (2006.01)

(52) U.S. Cl.
CPC .............. *A61F 2/24* (2013.01); *A61F 2/2475* (2013.01)

(58) Field of Classification Search
CPC ................................ A61F 2/24; A61F 2/2475
See application file for complete search history.

(56) References Cited

U.S. PATENT DOCUMENTS 5,595,571 A * 1/1997 Jaffe .................... A61L 27/3604
                                                      623/2.13
5,679,005 A   10/1997 Einstein
6,018,096 A    1/2000 Keating et al.
(Continued)

OTHER PUBLICATIONS

Hoppe, Hanno et al., "Percutaneous Technique for Creation of Tricuspid Regurgitation in an Ovine Model," J. Vasc. Interv. Radio., 18:133-136, 2007.
(Continued)

*Primary Examiner* — Thomas J Sweet
*Assistant Examiner* — Tiffany Shipmon
(74) *Attorney, Agent, or Firm* — Buchanan Van Tuinen LLC

(57) ABSTRACT

Animal models useful in the evaluation of medical devices, such as intraluminal medical devices, including intraluminal valve prostheses, are described. An example animal model comprises an animal in which a chordae tendineae attached to at least one of the leaflets of the tricuspid valve has been cut during an interventional procedure. Methods of evaluating intraluminal medical devices are also described. An example methods comprises cutting chordae tendineae attached to a leaflet of a tricuspid valve of an animal; allowing the animal to recover from the step of cutting the chordae tendineae; implanting an intraluminal medical device at a target site within a body vessel of the animal; allowing the animal to recover from the step of implanting an intraluminal medical device; and monitoring in vivo performance of the intraluminal medical device.

13 Claims, 4 Drawing Sheets

(56) References Cited

U.S. PATENT DOCUMENTS

| | | | |
|---|---|---|---|
| 6,355,030 B1* | 3/2002 | Aldrich | A61B 18/08 |
| | | | 606/28 |
| 6,444,872 B1 | 9/2002 | Andersson et al. | |
| 6,580,016 B2 | 6/2003 | Teirstein et al. | |
| 6,924,413 B2 | 8/2005 | Katsuyama | |
| 7,798,815 B2 | 9/2010 | Ramphal et al. | |
| 8,709,076 B1* | 4/2014 | Matheny | A61F 2/2418 |
| | | | 623/2.1 |
| 2004/0268421 A1 | 12/2004 | Tearney et al. | |
| 2008/0187895 A1 | 8/2008 | Sakezles | |

OTHER PUBLICATIONS

Bai, Yuan, et al., "Percutaneous establishment of tricuspid regurgitation: an experimental model for transcatheter tricuspid valve replacement," Chin. Med. J. 123(7): 806-809, 2010.

Kinney, et al., "Acute, reversible tricuspid insufficiency: creation in canine model," Am. J. Physiol. Heart Circ. Physiol. 260, 638-641, 1991.

* cited by examiner

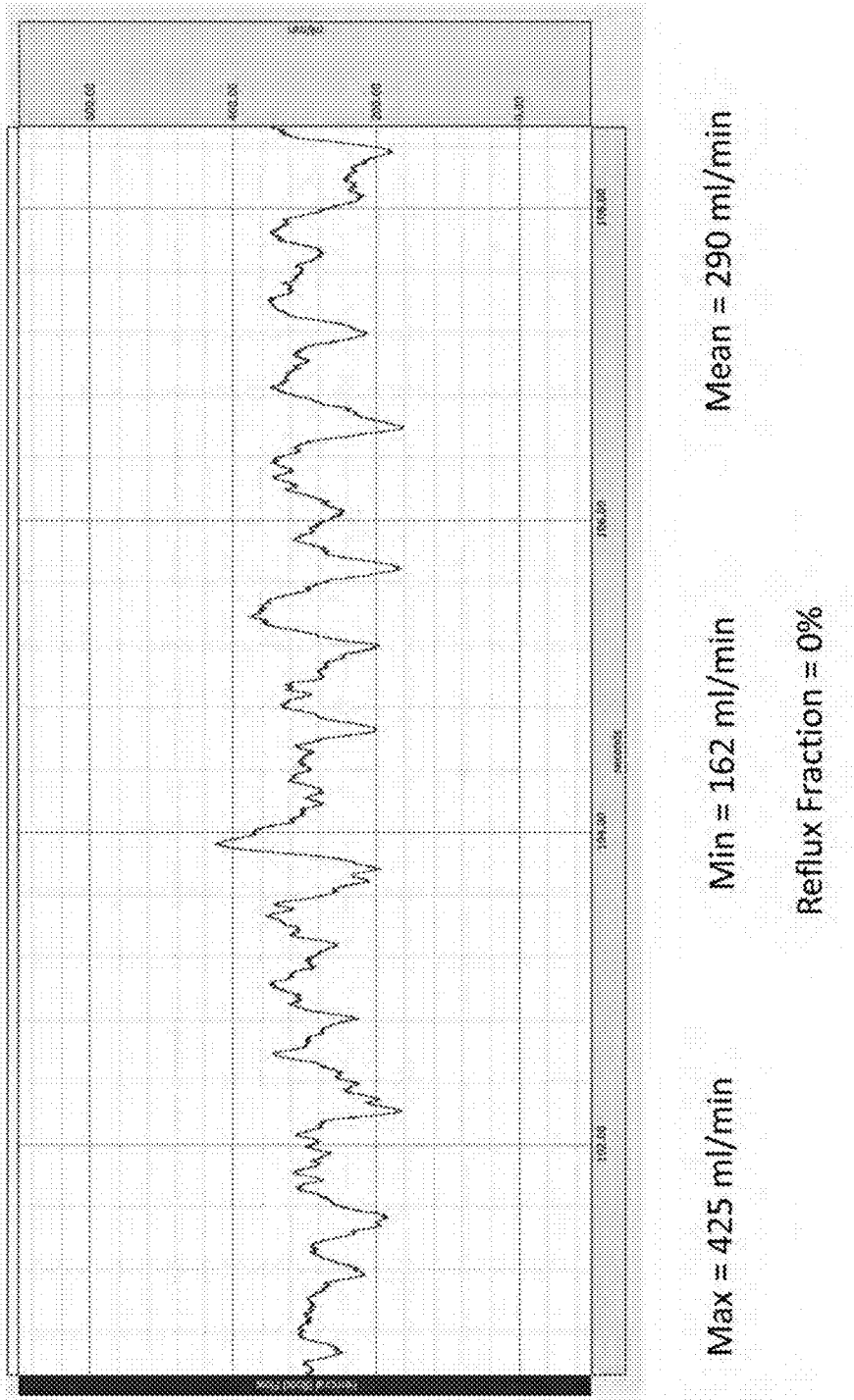

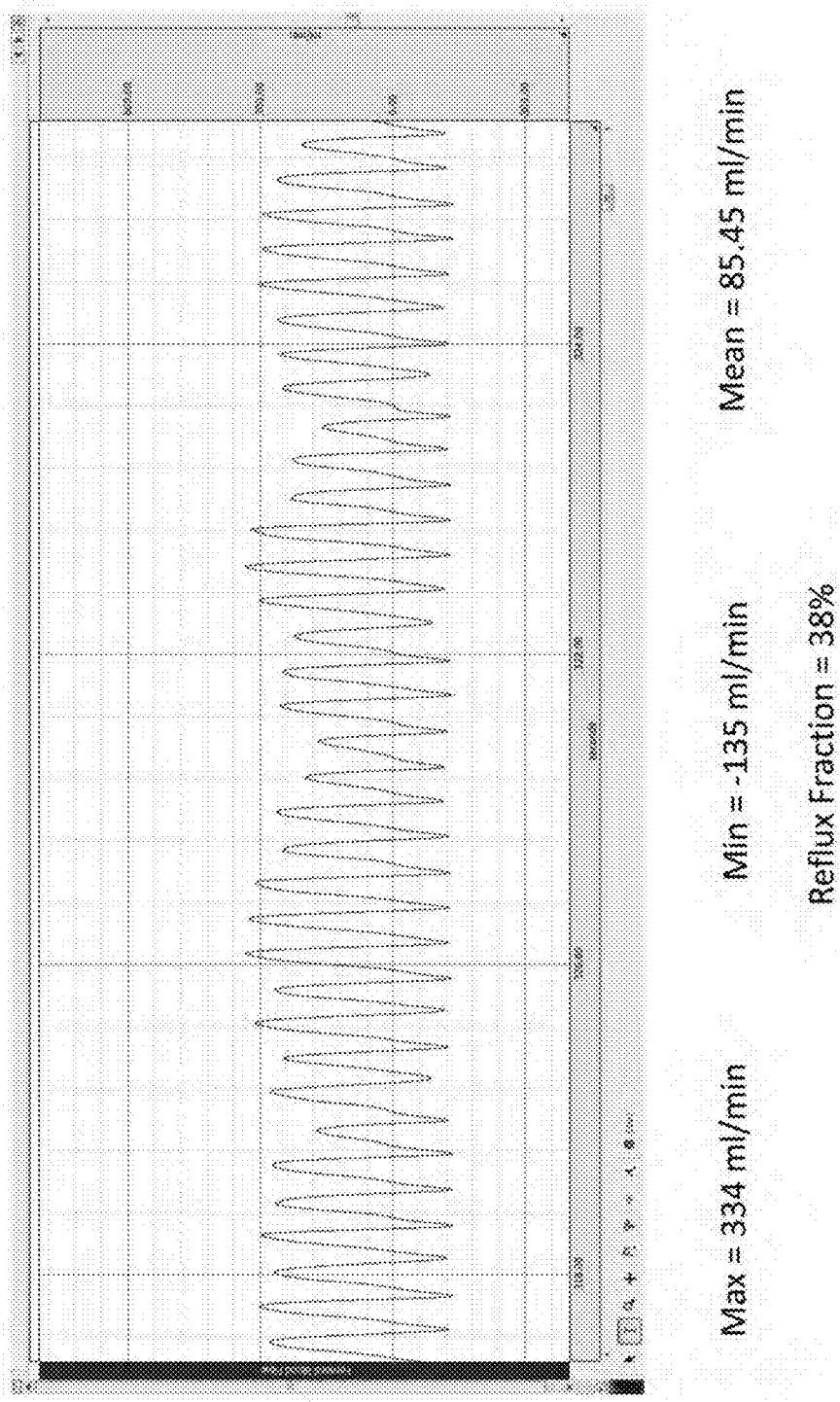
FIG. 2 - Femoral Blood Flow: Chordae Tendineae cut, Pre-Implant of Intraluminal Venous Valve Prosthesis

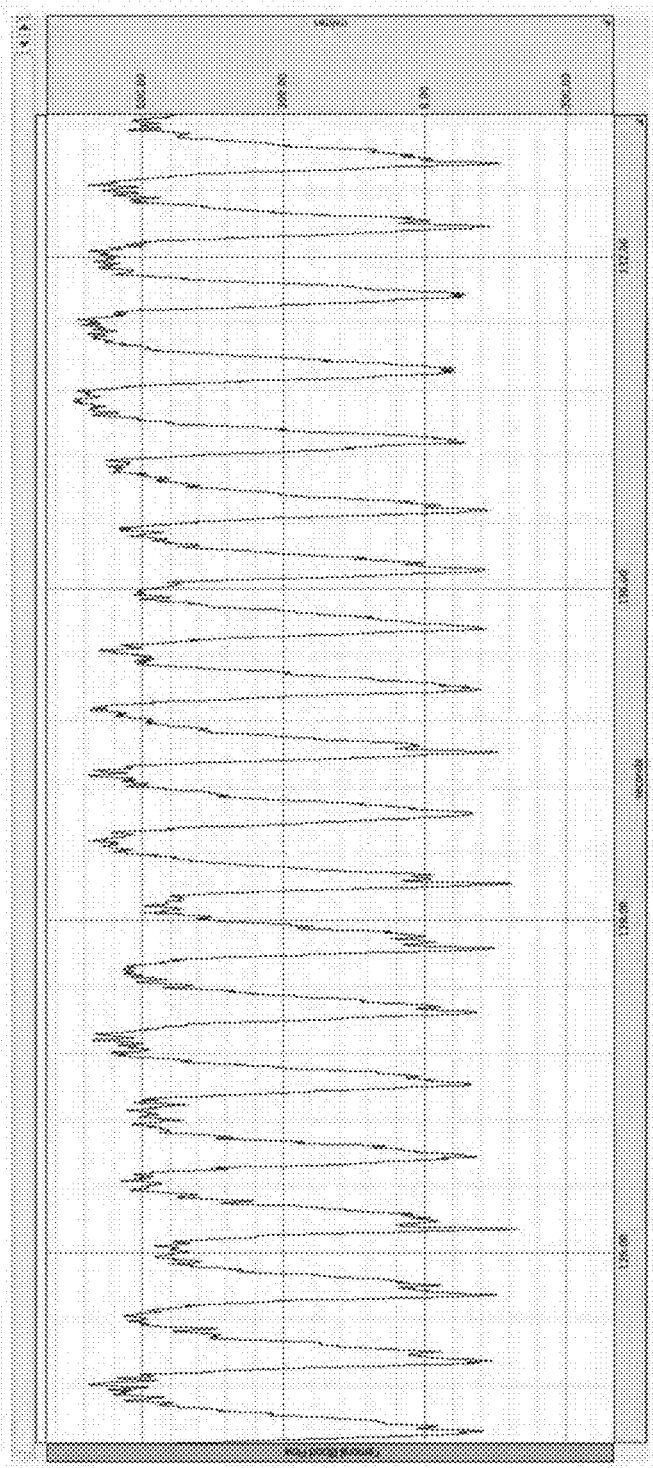
FIG. 3 - Femoral Blood Flow: Chordae Tendineae cut, Post-Implant of Intraluminal Venous Valve Prosthesis
Max = 741 ml/min    Min = -194 ml/min    Mean = 376 ml/min
Reflux Fraction = 4.1%

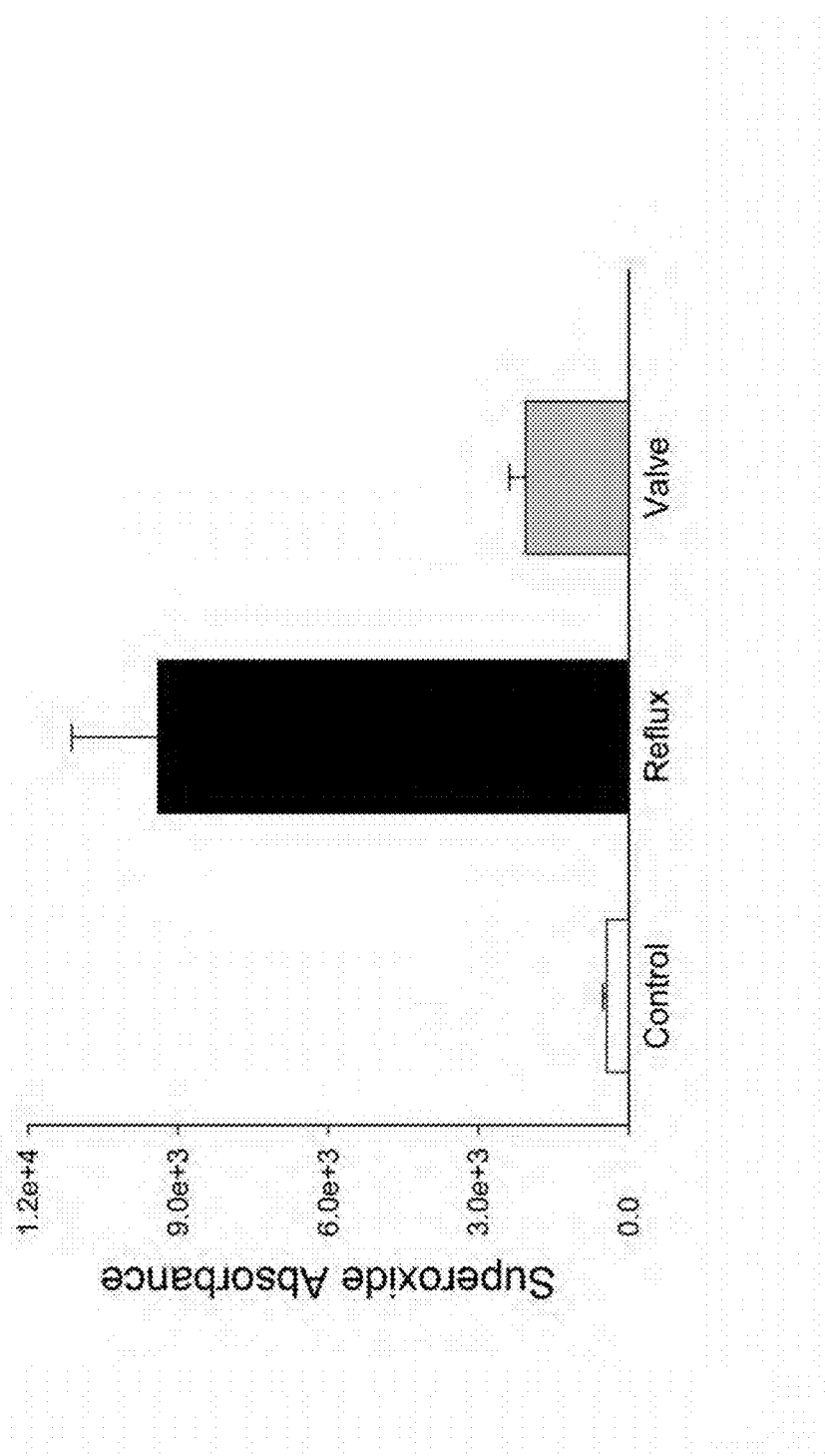

TRICUSPID REGURGITATION MODEL AND METHODS OF EVALUATING INTRALUMINAL MEDICAL DEVICES

FIELD

The disclosure relates to the creation of an animal model based on tricuspid valve injury that creates a reverse flow velocity and pressure gradient to facilitate dynamic valve function when a valve device is under evaluation. The animal model is useful in the evaluation of medical devices, such as valve prostheses. The disclosure also relates to methods of evaluating medical devices.

BACKGROUND

Previous attempts at designing implantable venous valve prostheses have relied on a healthy sheep animal model in which the devices are implanted within the jugular vein. Investigators have also used healthy animal canine, porcine and bovine models with jugular and iliac vein implant sites. Questions remain, though, about whether these animal models provide a suitable hemodynamic environment for evaluating intraluminal medical devices intended for use in humans. For example, current animal models do not mimic the fluid dynamics of human veins. Specifically, the venous properties of humans are unique in that a reversal of flow opens and closes natural venous valves located within human veins. This reflux is attributable to the large hydrostatic column found in human veins. Quadrupeds lack such a hydrostatic gradient and, as a result, do not have degrees of reflux similar to humans.

Thus, a need remains for improved animal models useful in the evaluation of medical devices, including models useful in the evaluation of intraluminal medical devices, such as valve prostheses. A need also remains for improved methods of evaluating medical devices.

BRIEF OVERVIEW OF EXAMPLE EMBODIMENTS

Various example animal models and methods of evaluating medical devices are described and illustrated herein.

An example animal model comprises an animal in which the chordae tendineae attached to one or more leaflets of the tricuspid valve have been cut during an interventional procedure.

Another example animal model comprises an animal in which the chordae tendineae attached to the leaflets of the tricuspid valve have been cut during an interventional procedure and into which an intraluminal medical device has been implanted.

Another example animal model comprises a sheep in which the chordae tendineae attached to the leaflets of the tricuspid valve have been cut during an interventional procedure and into the iliac vein of which an intraluminal valve prosthesis has been implanted.

An example method of evaluating a medical device comprises cutting chordae tendineae attached to a leaflet of a tricuspid valve of an animal; allowing the animal to recover from the step of cutting the chordae tendineae; implanting an intraluminal medical device at a target site within a body vessel of the animal; allowing the animal to recover from the step of implanting an intraluminal medical device; and monitoring in vivo performance of the intraluminal medical device.

Another example method of evaluating a medical device comprises percutaneously cutting chordae tendineae attached to a leaflet of a tricuspid valve of an animal; allowing the animal to recover from the step of cutting the chordae tendineae; percutaneously implanting an intraluminal venous valve prosthesis at a target site within a vein of the animal; allowing the animal to recover from the step of implanting an intraluminal venous valve prosthesis; and monitoring in vivo performance of the intraluminal venous valve prosthesis.

Additional understanding of the inventive animal models and methods of evaluating can be obtained with review of the detailed description, below, and the appended drawings.

BRIEF DESCRIPTION OF THE DRAWINGS

FIG. 1 is a graphical representation of blood flow over time in an animal prior to cutting of chordae tendinae and implantation of an intraluminal venous valve prostheses.

FIG. 2 is a is a graphical representation of blood flow over time in the animal represented in FIG. 1 after cutting of chordae tendinae and before implantation of an intraluminal venous valve prosthesis.

FIG. 3 is a is a graphical representation of blood flow over time in the animal represented in FIG. 1 after cutting of chordae tendinae and implantation of an intraluminal venous valve prosthesis.

FIG. 4 is a graphical representation of results of a superoxide assay on control animals (chordae tendineae not cut), reflux animals (chordae tendinae cut), and valve animals (chordae tendinae cut and intraluminal venous valve prosthesis implanted in a body vessel of the animal).

DETAILED DESCRIPTION OF EXAMPLE EMBODIMENTS

The following detailed description and the appended drawings describe and illustrate various example animal models and methods of evaluating medical devices that are embodiments of the invention. The description and drawings are exemplary in nature and are provided to enable one skilled in the art to make and use one or more animal models and one or more methods of evaluating medical devices in accordance with the invention. The description and drawings are not intended to limit the scope of the claims in any manner.

As used herein, the term "cut," and grammatically related terms, refers to disruption of a continuous member into separate member portions. The term does not require the use of any particular tool or type of tool to achieve the disruption. Furthermore, the term does not require any particular motion or action to achieve the disruption.

Inventive animal models are described. The animal models are useful in the evaluation of intraluminal medical devices, including valve prostheses. As such the animal model may be useful in the design and development of effective intraluminal medical devices, including implantable venous valve prostheses and other valve devices. The animal models also may be useful for other purposes, including investigations into inflammatory mediators of venous disease, indentification of biomarkers of venous disease, and other purposes.

The inventors have determined that a healthy animal model, including those used previously in in vivo evaluations of implantable valve devices, does not provide a hemodynamic environment that requires valve leaflet motion. As such, valve devices implanted in the target vessel of healthy animals according to these models tended to be walled off with a fibrous or neointimal capsule. Eventually, and sometimes immediately after implantation, implanted valve devices demonstrated a lack of dynamic valve function, which was attributed to the lack of reflux required to sustain valve function and ultimately resulted in thrombosis. The inventors determined that hemostasis occurring within particular regions of valve devices implanted in healthy animals, such as within valve sinus regions, was reflective of an insufficient degree of reflux.

To overcome these drawbacks of existing animal models, the inventive animal model includes an induced injury that creates a physiologically relevant reverse flow velocity and pressure gradient to facilitate dynamic valve function when a valve device is under evaluation. The animal model comprises an animal in which a chordae tendineae attached to at least one of the leaflets of the tricuspid valve have been cut during an interventional procedure. An intraluminal medical device can be implanted into an animal treated in this way to create an animal model useful for evaluating the intraluminal medical device in vivo.

Any suitable animal can be used and a skilled artisan will be able to select an appropriate animal based on various considerations, including the size of the intraluminal medical device for the evaluation of which the animal is being used. For venous valve devices, the inventors have determined that canines are suitable for use in the animal models and methods. Examples of other suitable animals include sheep, cows, horses, pigs, cats and other animals. As such, the inventive animal models include canine, ovine, bovine, equine, porcine, feline and other animal models.

Any suitable interventional technique, device and/or equipment can be used to cut the chordae tendineae attached to the leaflets of the tricuspid valve in a selected animal, and a skilled artisan will be able to select an appropriate technique, device and/or equipment for cutting the chordae tendineae in a particular animal based on various considerations, including the relative ease with which the chordae tendineae can be accessed through various different routes. Open surgical techniques, including transthoracic and other approaches, are considered suitable. For these procedures, conventional methods and devices, including scalpels, can be used to access and cut the chordae tendinae. Percutaneous techniques, in which access is gained via a percutaneous puncture and passage of one or more devices through the puncture opening, are also considered suitable. Transvascular techniques, which include navigation of one or more devices through a vessel, such as a vascular vessel, following entry through a puncture, are also considered suitable. For transvascular techniques, an elongate cutting device capable of being navigated through a body vessel, such as with an intraluminal catheter, can be used to cut the chordae tendineae. The cutting devices described in U.S. Provisional Application for Patent No. 61/929,652 to Krieger et al., filed on Jan. 21, 2014, for CUTTING DEVICES AND METHODS are considered suitable for cutting the chordae tendineae when a transvascular technique is used to access the chordae tendineae. Also, the cutting devices described in U.S. Non-Provisional Application for patent Ser. No. 14/600,336 to Krieger et al., filed on Jan. 20, 2015, for CUTTING DEVICES AND METHODS are considered suitable for cutting the chordae tendineae when a transvascular technique is used to access the chordae tendineae. Each of these applications is hereby incorporated into this disclosure in its entirety for the purposes of describing suitable cutting devices and methods for cutting the chordae tendineae. Also, any suitable route of access to the chordae tendineae can be used when a transvascular technique is used to access and cut the chordae tendineae, including jugular and femoral approaches.

Any suitable number of chordae tendineae can be cut, including a single chordae tendineae, two chordae tendineae, three chordae tendineae, and more than three chordae tendineae. The number of chordae tendineae cut in a particular procedure will depend on various considerations, including the degree of reflux desired for the study for which the animal model is intended. Furthermore, the total number of chordae tendineae cut in a particular procedure can be attached to a single leaflet of the tricuspid valve of the animal, or can be attached to different leaflets of the tricuspid valve. For example, the total number of chordae tendineae can include chordae tendineae attached to only a single leaflet of the tricuspid valve of the animal, chordae tendineae attached to two different leaflets of the tricuspid valve of the animal, or chordae tendineae attached to three different leaflets of the tricuspid valve of the animal. This provides another level of control over the level of reflux generated in the model. A skilled artisan will be able to determine both a total number of chordae tendineae to be cut and a distribution of the chordea tendineae being cut relative to the leaflets of the tricuspid valve for a particular procedure to provide a desired level of reflux in the animal model.

If multiple chordae tendineae are being cut in a particular procedure, the chordae tendineae can be cut individually or in groups of two or more. Furthermore, if multiple cutting steps are conducted, hemodynamic measurements, such as venous pressure and reflux, can be taken in between cutting steps to assess whether a desired level of reflux has been achieved. If the measurements indicate that a desired level has not been achieved by the cuts that have already been performed, additional chordae tendineae can be cut. This cycle of cutting chordae tendineae and taking hemodynamic measurements can be repeated until the measurements indicate that a desired level of reflux has been achieved.

The chordae tendineae on any leaflet of the tricuspid valve of the animal in a particular procedure can be cut. In some procedures, it may be desirable to cut chordae tendineae on a particular leaflet of the tricuspid valve. Indeed, in some procedures, it may be desirable to cut chordae tendineae on only a particular leaflet. For example, the septal leaflet is generally the smallest leaflet of the tricuspid valve and usually has the smallest number of chordae tendineae. If a relatively low degree of reflux is desired for a particular animal model, it may be advantageous to cut the chordae tendineae attached to the septal leaflet first as cutting of additional chordae tendineae attached to the other leaflets may not be necessary. On the other hand, if a relatively high degree of reflux is desired for a particular animal model, it may be advantageous to cut the chordae tendineae attached to one or both of the anterior and posterior leaflets. Targeting the chordae tendineae on these leaflets can prevent right ventricle free wall compensation while sustaining sufficient forward pulmonic blood flow as preserved via septal leaflet integrity. Ultimately, the degree of reflux desired in a particular animal can be obtained through various combinations of partial or complete avulsion of individual leaflets of the tricuspid valve, accomplished by cutting none, some or all of the chordae tendineae associated with each of the leaflets.

The chordae tendineae of the tricuspid valve can be cut to any degree, including partial and complete severing of the chordae tendineae. The inventors have determined that a complete severing of each chordae tendineae being cut produces an environment with desirable characteristics for evaluating prosthetic venous valve devices.

As an alternative to cutting the chordae tendineae directly, the chordae tendineae, and/or the leaflet of the tricuspid valve to which it is attached, can be pulled, without cutting, to cause a disruption of the papillary muscle sufficient to produce regurgitation.

The inventors have determined that the introduction of reflux into the vascular system of the animal by cutting chordae tendineae causes the animal to be in a hyperinflammatory state on the venous side of the circulatory system. Significant inflammation occurs in the veins of animals treated in this manner, making the animal model reflective of venous disease in humans, which is marked by considerable inflammation in the veins. Furthermore, this condition makes the animal model particularly well suited for evaluating medical devices intended to be used in treatment of venous disease in humans, including intraluminal venous valve prostheses.

Any suitable intraluminal medical device can be used and a skilled artisan will be able to select an appropriate intraluminal medical device based on various considerations, including the nature of the medical device for which the animal model is intended to serve as a model for evaluation. The inventors have determined that intraluminal valve devices, including intraluminal venous valve devices that comprise one or more leaflets attached to an expandable support frame, are suitable for use in the animal models described herein. Examples of other intraluminal medical devices considered suitable for use in the animal models described herein include self-expandable intraluminal medical devices; intraluminal medical devices that require an input of force to affect radial expansion; including balloon expandable intraluminal medical devices; heart valve devices; tissue valve devices; stents; stent-graft devices; endografts; filters; occluders; catheters; guidewires; scopes; and other intraluminal and other implantable medical devices.

The intraluminal medical device can be implanted using any suitable interventional technique, device and/or equipment. A skilled artisan will be able to select appropriate technique(s), device(s) and/or equipment for implanting the intraluminal medical device in a particular animal based on various considerations, including the relative ease with which the target implant site can be accessed through various different routes. Both surgical and percutaneous techniques for implanting an intraluminal medical device are considered suitable. Scalpels and other conventional or later-developed cutting devices can be used to facilitate implantation when a surgical technique is used to implant the intraluminal medical device. Catheters, guidewires, and other conventional or later-developed devices can be used to facilitate implantation when a percutaneous technique is used to implant the intraluminal medical device.

The intraluminal medical device can be implanted in any suitable location within the animal. A skilled artisan will be able to select an appropriate location in a particular animal based on various considerations, including the intended bodily location and/or environment into which the intraluminal medical device is intended to be used in other animals, including humans. The inventors have determined that, for intraluminal valve devices intended to be implanted intraluminally within humans, an intraluminal implantation in the animal model provides desirable conditions for evaluating the intraluminal valve devices. Furthermore, for intraluminal venous valve prostheses, the inventors have determined that implantation in the venous system of the animal model provides desirable conditions for evaluating the intraluminal venous valve prostheses. In particular, the inventors have determined that implantation of an intraluminal venous valve prosthesis in the iliac vein provides desirable conditions for evaluating the intraluminal venous valve prostheses. The inventors have determined that the iliac vein of an ovine animal model, as described herein, provides desirable conditions for evaluating the intraluminal venous valve prostheses.

When creating a tricuspid regurgitation model in an animal or when performing a method of evaluating an intraluminal medical device according to an embodiment, additional steps, techniques, procedures can be included. For example, it may be desirable to place an animal being used on an anti-coagulation regimen over a portion or the entirety of the study being performed. If included, any suitable anti-coagulation regimen can be used and the particular regimen chosed for a particular study will depend on various considerations, including the type of animal used and the nature of the intraluminal device under evaluation, if appropriate. As an example, the inventors have used a Coumadin anti-coagulation regimen when using canines in the creation of the tricuspid regurgitation model and in methods of evaluating intraluminal medical devices, including intraluminal valve prostheses. Other anti-coagulation regimens that may be suitable include a dual antiplatelet therapy (DAPT) using aspirin and clopidogrel. Furthermore, it may be desirable to place an animal being used on a heart failure pharmacological management regimen over a portion or the entirety of the study being performed. For example, it may be desirable to place a subject animal on a beta block regimen over a portion or the entirety of the study being performed.

Example 1—Tricuspid Regurgitation Model

This example describes a basic procedure for creating the tricuspid regurgitation model in an animal.

An initial step comprises sedating the animal. Sedation can be accomplished using conventional procedures and materials considered suitable for the animal used.

Another step comprises cutting the chordae tendineae attached to a leaflet of the tricuspid valve of the animal. This step can be performed using any suitable open surgical, percutaneous or transvascular technique. This step can be conducted under suitable visualization to monitor the cutting of the chordae tendineae. Examples of suitable visualization techniques include, but are not limited to, conventional fluoroscopy and ultrasound visualization, including echocardiography. The inventors have determined that the use of echocardiography is particularly advantageous because it enables visualization of individual chordae tendineae and papillary muscles, which can facilitate the cutting of the chordae tendineae.

Another step comprises allowing the animal to recover from the step of cutting the chordae tendineae. For this step, allowing the animal to recover comprises allowing a period of time to pass between the step of cutting the chordae tendineae and any subsequent treatment steps. For canines, the inventors have determined that a recovery period of at least two weeks is suitable.

Example 2—Tricuspid Regurgitation Model and Evaluation of an Implanted Medical Device This example describes a basic method for evaluating an intraluminal medial device and includes the basic procedure for treating an animal to create the tricuspid regurgitation model and an implantation of the intraluminal medical device to be evaluated.

An initial step comprises sedating the animal. Sedation can be accomplished using conventional procedures and materials considered suitable for the animal used.

Another step comprises cutting the chordae tendineae attached to the leaflets of the tricuspid valve. This step can be performed using any suitable open surgical, percutaneous or transvascular technique. This step can be conducted under suitable visualization to monitor the cutting of the chordae tendineae. Examples of suitable visualization techniques include, but are not limited to, conventional fluoroscopy and ultrasound visualization.

Another step comprises allowing the animal to recover from the step of cutting the chordae tendineae. For this step, allowing the animal to recover comprises allowing a suitable period of time to pass between the step of cutting the chordae tendineae and the step of implanting an intraluminal medical device. For canines, the inventors have determined that a recovery period of at least two weeks is suitable.

Another step comprises sedating the animal after the step of allowing the animal to recover. As with the initial step, sedation can be accomplished using conventional procedures and materials considered suitable for the animal used Another step comprises implanting an intraluminal medical device at a target site within a body vessel of the animal. For this step, implantation can be performed using any suitable technique, including open surgical, percutaneous and transvascular techniques. A skilled artisan can select a suitable technique chosen for a specific intraluminal medical device based on various considerations, including the nature of the intraluminal medical device being implanted and the target site at which the intraluminal medical device will be implanted. This step can be conducted prior to, concurrently with, or following the step of cutting of the chordae tendineae.

Another optional step comprises allowing the animal to recover from the step of implanting an intraluminal medical device. For this step, allowing the animal to recover comprises allowing a suitable period of time to pass between the step of implanting an intraluminal medical device and the step of monitoring in vivo performance of the intraluminal medical device. For canines and methods of evaluating intraluminal venous valve prostheses, the inventors have determined that this step is not necessary and that a monitoring step can be performed immediately following the implanting step, or shortly thereafter.

Another step comprises monitoring in vivo performance of the intraluminal medical device. Monitoring can comprise various assessments, including qualitative and quantitative assessments of the performance of the intraluminal medical device, direct or indirect measurements of the intraluminal medical device and/or the environment at the target site, and direct or indirect visualization of the intraluminal medical device. A skilled artisan will be able to select suitable assessments for a particular method based on various considerations, including the nature and intended function of the intraluminal medical device being evaluated. For intraluminal valve prostheses, the inventors have determined that direct visualization of valve performance and quantitative hemodynamic measurements, such as fluid pressures and flow rates, are suitable.

Example 3—Animal Treatment and Evaluation of an Intraluminal Venous Valve Prosthesis This example describes a basic method for evaluating an intraluminal venous valve prosthesis and includes a version of the basic procedure for treating an animal to create the tricuspid regurgitation model and an implantation of the intraluminal venous valve device to be evaluated.

In an initial step, anesthesia and intubation are performed on the animal.

In another step, a percutaneous insertion of a jugular vein catheter is performed.

In another step, measurement of baseline hemodynamics (pressure, duplex, echocardiography) is performed.

In another step, cutting of a single right tricuspid chordae under fluoroscopic and/or echocardiographic guidance is performed. In this step, a chordae attached to a particular leaflet can be targeted based on a desired degree of reflux, as described above. In this particular example, an elongate wire member with a cutting edge, as noted above, is advanced slightly past the valve opening and then manipulated to sweep the cutting edge into engagement with a chordae tendinae to be cut. With further and/or continued manipulation of the wire member, the engagement between the cutting edge and the chordae tendineae leads to a cutting of the chordae tendineae.

In another step performed after the chordae tendineae is cut, another measurement of hemodynamics (pressure, duplex, echocardiography) is performed.

The cutting and post-disruption measurement steps can be repeated until desired a level of reflux is obtained based on relationship between right atrial pressure (RAP) and jugular venous pressure (JVP) or via direct reflux assessment with duplex US.

In another step, the catheter is removed and animal recovered for 1-2 weeks with hemodynamic evaluation using duplex and echocardiography performed at regular intervals.

Another step comprises sedating the animal after the animal recovers. As with the initial step, sedation can be accomplished using conventional procedures and materials considered suitable for the animal used Another step comprises implanting an intraluminal medical device at a target site within a body vessel of the animal. For this step, implantation can be performed using any suitable technique, including open surgical, percutaneous and transvascular techniques. A skilled artisan can select a suitable technique chosen for a specific intraluminal medical device based on various considerations, including the nature of the intraluminal medical device being implanted and the target site at which the intraluminal medical device will be implanted.

An optional step comprises allowing the animal to recover from the step of implanting an intraluminal medical device. For this step, allowing the animal to recover comprises allowing a suitable period of time to pass between the step of implanting an intraluminal medical device and the step of monitoring in vivo performance of the intraluminal medical device. For canines and methods of evaluating intraluminal venous valve prostheses, the inventors have determined that this step is not necessary and that a monitoring step can be performed immediately following the implanting step, or shortly thereafter.

Another step comprises monitoring in vivo performance of the intraluminal medical device. Monitoring can comprise various assessments, including qualitative and quantitative assessments of the performance of the intraluminal medical device, direct or indirect measurements of the intraluminal medical device and/or the environment at the target site, and direct or indirect visualization of the intraluminal medical device. A skilled artisan will be able to select suitable assessments for a particular method based on various considerations, including the nature and intended function of the intraluminal medical device being evaluated. For intraluminal valve prostheses, the inventors have determined that direct visualization of valve performance and quantitative hemodynamic measurements, such as fluid pressures and flow rates, are suitable.

Using this method, graded disruption of chordae can translate to an approximate reflux duration of >250 ms, including an approximate reflux duration of between about 250 ms and about 500 ms, reflux velocity of 15-30 cm/s and 10-40% peak reflux fraction. Assessment of intraluminal medical devices, including intraluminal venous valve prostheses, under these conditions demonstrate enhanced performance relative to pre-reflux conditions as indicated by reductions in reflux duration, velocity, and flow distal to the valve. Moreover, the induced venous reflux produces marked vascular inflammation which extends the applicability of this animal model to other vascular device testing. For example, reflux-induced inflammation can serve as a tool for assessing biomarkers in addition to vascular responses to stents, endografts, etc.

Example 4—Canine Animal Model Characterization

Canines were treated as described herein to create a canine animal model useful in the evaluation of medical devices, such as intraluminal medical devices, including intraluminal valve prostheses. To characterize the animal model, femoral blood flow was measured at various times during the treatment of the animal to assess vascular reflux. Also, a controlled superoxide assay was performed to assess inflammation in the animal.

FIG. 1 is a graphical representation of blood flow over time in an animal prior to cutting of chordae tendinae and implantation of an intraluminal venous valve prostheses.

FIG. 2 is a is a graphical representation of blood flow over time in the animal represented in FIG. 1 after cutting of chordae tendinae and before implantation of an intraluminal venous valve prosthesis.

FIG. 3 is a is a graphical representation of blood flow over time in the animal represented in FIG. 1 after cutting of chordae tendinae and implantation of an intraluminal venous valve prosthesis.

Baseline superoxide measurements (no reflux) were obtained from intact control canines that had not been treated as described herein to induce regurgitation. Immediately following euthanasia, the common femoral vein was excised and placed into a 37° C. HEPES filled conical tube. Similarly, valve and contralateral control (no valve) femoral veins were obtained from canines subjected to 8 weeks of venous reflux induced by cutting of chordae tendineae as described herein.

The harvested vessels were placed into 37° C. HEPES filled dish, removed of their adventitia and cut into 9 rings of approximately 2 mm in length (3 rings per treatment). The rings were transferred into a 37° C. HEPES-filled 96 well plate into an upright position. 100 µM of chemiluminescence, L-012, was added to 3 rings just before placed into Perkin Elmer (En vision Xcite Multilabel Reader, Perkin Elmer, Shelton, Conn.) plate reader. The total reaction volume was 200 µl. The luminescence was recorded for 60 minutes at 1 minute intervals. At the end of the experiment, rings were air-dried, weighed and data normalized to respective tissue weight.

As illustrated in FIG. 4, compared to baseline control measurements (Control), superoxide production was significantly elevated (P=0.02) in veins exposed to 8 weeks of venous reflux (Reflux). Importantly, this increase was attenuated to near control values in veins distal to venous valve implantation (Valve) (P=0.304 vs. Control). These findings support that endothelial/venous dysfunction corresponds with elevations in superoxide production and that implantation of the intraluminal venous valve prosthesis markedly attenuates these adverse vascular outcomes.

The foregoing detailed description refers to examples and includes the best mode for practicing the invention. The description and the appended drawings are intended only to provide examples and not to limit the scope of the claims in any manner.

What is claimed is:

1. A method of evaluating an intraluminal medical device, the method comprising:
    cutting chordae tendineae attached to a leaflet of a tricuspid valve of an animal;
    allowing the animal to recover from the step of cutting the chordae tendineae;
    implanting an intraluminal medical device at a target site within a body vessel of the animal;
    allowing the animal to recover from the step of implanting an intraluminal medical device; and
    monitoring in vivo performance of the intraluminal medical device.

2. The method of claim 1, wherein the animal comprises a sheep.

3. The method of claim 1, wherein the step of cutting chordae tendineae comprises accessing the chordae tendineae percutaneously.

4. The method of claim 1, wherein the step of cutting chordae tendineae comprises accessing the chordae tendineae surgically.

5. The method of claim 1, wherein the step of implanting an intraluminal medical device comprises percutaneously implanting an intraluminal medical device.

6. The method of claim 1, wherein the step of implanting an intraluminal medical device comprises surgically implanting an intraluminal medical device.

7. The method of claim 1, wherein the intraluminal medical device comprises an intraluminal valve prosthesis.

8. The method of claim 1, wherein the intraluminal medical device comprises an intraluminal venous valve prosthesis.

9. The method of claim 1, wherein the step of implanting an intraluminal medical device is conducted prior to the step of cutting chordae tendineae.

10. The method of claim 1, wherein the step of implanting an intraluminal medical device is conducted concurrently with the step of cutting chordae tendineae.

11. The method of claim 1, wherein the step of implanting an intraluminal medical device follows the step of cutting chordae tendineae.

12. A method of evaluating an intraluminal medical device, the method comprising:
    cutting chordae tendineae attached to a leaflet of a tricuspid valve of an animal;
    allowing the animal to recover from the step of cutting the chordae tendineae;
    implanting an intraluminal medical device at a target site within a body vessel of the animal;
    allowing the animal to recover from the step of implanting an intraluminal medical device; and
    monitoring in vivo performance of the intraluminal medical device;

wherein the step of allowing the animal to recover from the step of cutting chordae tendineae comprises allowing at least two weeks to pass between the step of cutting chordae tendineae and any subsequent step.

13. The method of claim 12, wherein the step of allowing the animal to recover from the step of cutting chordae tendineae comprises allowing at least two weeks to pass between the step of cutting chordae tendineae and the step of implanting an intraluminal medical device.

* * * * *